United States Patent [19]
Garavaglia et al.

[11] Patent Number: 5,620,788
[45] Date of Patent: Apr. 15, 1997

[54] WETTABLE POLYMERIC FABRICS WITH DURABLE SURFACTANT TREATMENT

[75] Inventors: Arthur E. Garavaglia, Alpharetta; John G. MacDonald, Decatur; Ronald S. Nohr; Cheryl A. Perkins, both of Roswell, all of Ga.

[73] Assignee: Kimberly-Clark Corporation, Neenah, Wis.

[21] Appl. No.: 93,291

[22] Filed: Jul. 16, 1993

Related U.S. Application Data

[63] Continuation-in-part of Ser. No. 978,605, Nov. 19, 1992, abandoned.

[51] Int. Cl.$^6$ .................................................. B32B 27/00
[52] U.S. Cl. .................. 442/118; 252/8.61; 428/447; 604/358; 604/367; 604/378; 604/385.1; 442/170
[58] Field of Search .................... 428/289, 290, 428/286, 288, 446, 447; 252/8.8, 8.9; 604/358, 367, 385.1, 378, 913

[56] References Cited

U.S. PATENT DOCUMENTS

| | | | |
|---|---|---|---|
| 5,057,361 | 10/1991 | Sayovitz et al. | 428/290 |
| 5,079,076 | 1/1992 | Lal | 428/224 |
| 5,079,081 | 1/1992 | Lal | 428/290 |
| 5,101,012 | 3/1992 | Lal | 528/337 |
| 5,209,966 | 5/1993 | Lange et al. | 428/272 |
| 5,212,270 | 5/1993 | Lal | 526/287 |

FOREIGN PATENT DOCUMENTS

| | | | |
|---|---|---|---|
| 0288620 | 11/1988 | European Pat. Off. | D06M 13/16 |
| 2343078 | 9/1977 | France | D06M 15/00 |
| 289179 | 11/1990 | Japan . | |
| WO91/14042 | 9/1991 | WIPO . | |
| WO91/14043 | 9/1991 | WIPO . | |
| WO91/14041 | 9/1991 | WIPO . | |
| WO91/14040 | 9/1991 | WIPO . | |

*Primary Examiner*—D. S. Nakarani
*Attorney, Agent, or Firm*—William D. Herrick

[57] ABSTRACT

A polymeric fabric having enhanced wettability, a method for producing such wettable polymeric fabric, and a composition for use in the method. The polymeric fabric is preferably a nonwoven. In one embodiment, the fabric includes a succinate surfactant substantially uniformly distributed on the surface of the fabric. The succinate surfactant is applied with a co-wetting aid which reduces the surface tension of the surfactant composition. In another embodiment, the polymeric fabric comprises multiple surfactants on the surface of the polymeric fabric. The first surfactant has a cloud point less than 50° C. and a low solubility in water and is dispersible in water. The second surfactant comprises a succinate surfactant. The first and second surfactants are applied to the fabric in an aqueous solution preferably with a co-wetting aid such as a primary or secondary alcohol. The co-wetting aid wets the polymeric fabric with the composition during application of the composition to the polymeric fabric and then evaporates.

10 Claims, 3 Drawing Sheets

WETTABLE POLYMERIC FABRICS WITH DURABLE SURFACTANT TREATMENT

CROSS-REFERENCE

This application is a continuation-in-part of U.S. patent application Ser. No. 07/978,605 filed with the U.S. Patent Office on Nov. 19, 1992, now abandoned.

TECHNICAL FIELD

This invention generally relates to polymeric fabrics, and more particularly, relates to surface treatments for improving the wettability of polymeric fabrics.

BACKGROUND OF THE INVENTION

Polymeric fabrics are used to make a variety of products, including water-absorbent articles. Such products include towels, wipes, and absorbent personal care products including infant care items such as diapers, child care items such as training pants, feminine care items such as sanitary napkins, and adult care items such as incontinence products. Polyolefin nonwoven fabrics are particularly suited for making these type products.

Water-absorbent articles, especially personal care absorbent articles, desirably include a nonwoven polymeric fabric which provides rapid intake of fluid such as water or an aqueous solution, minimal spreading of fluid on the fabric surface before fluid penetration, and wettability which is durable enough to survive multiple fluid insults. However, polyolefin nonwoven fabrics and other types of polymeric fabrics are normally water-repellent. Thus, to effectively absorb water, the polymeric fabrics must be treated to become hydrophilic.

One method of making polymeric fabrics more wettable is applying a surfactant to the surface of the fabric. Conventional surfactants for treating polymeric fabrics include non-ionic surfactants such as octylphenoxypolyethoxy ethanol. Although such conventional surface treatments are effective to make polymeric fabrics wettable, there are still some problems. For example, conventional surface treatment compositions such as the foregoing are relatively easily rubbed-off the fabric and are also easily washed-off the fabric when the fabric is wetted. Such surface treatments are often substantially completely removed from the polymeric fabric after only one liquid insult or washing. After the surface treatment is removed, the polymeric fabric again becomes water-repellent and less effective to absorb water. Moreover, to compensate the inability of conventional surface treatments to survive use, conventional surface treatments are often applied to primary fabrics in large quantities and thus the cost of the treated fabric is increased.

U.S. Pat. No. 5,057,361 to Sayovitz et al. discloses a durable surface treatment for improving the wettability of polymeric fabrics. That patent discloses the treatment of polymeric fabric with a primary surfactant having a low solubility in water. The primary surfactant is applied to the fabric in an aqueous solution along with a fugitive co-surfactant or co-wetting aid which is functional to wet the polymeric fabric during application of the primary surfactant and provides for substantially uniform distribution of the primary surfactant onto the fabric.

Although the surface treatment disclosed in U.S. Pat. No. 5,057,361 is an effective and durable surface treatment for improving the wettability of polymeric fabrics, there is still a need an even more durable surface treatment for improving the wettability of polymeric fabrics.

SUMMARY OF THE INVENTION

Accordingly, an object of the present invention is to provide an improved polymeric fabric.

Another object of the present invention is to provide a polymeric fabric having enhanced wettability.

A further object of the present invention is to provide a polymeric fabric that rapidly absorbs fluid with minimal spreading of fluid on the surface of the fabric before the fluid penetrates into the fabric.

Still another object of the present invention is to provide a surface treatment that enhances the wettability of polymeric fabrics and survives multiple wash cycles.

Accordingly, the present invention provides a polymeric fabric with a succinate surfactant on the surface of the fabric. The present invention also comprehends processes for applying the succinate surfactant to the polymeric fabric in an aqueous solution and compositions which, when applied to the polymeric fabric, increase the wettability of the polymeric fabric.

According to one embodiment of the present invention, a wettable polymeric fabric comprises a normally water repelling fabric and sorbitol succinate surfactant substantially uniformly distributed on the surface of the fabric. Suitable succinate surfactants include ethoxylated amino sorbitol succinate salt and alkenyl succinate anhydride ethoxylated fatty amine salt. The succinate surfactant is substantially uniformly distributed on the surface of the polymeric fabric by a process wherein the succinate surfactant is applied to the surface of the fabric in an aqueous composition comprising a co-wetting aid. The co-wetting aid reduces the surface tension of the aqueous composition and is present in an amount sufficient so that the surfactant is uniformly distributed on the surface of the polymeric fabric during application of the aqueous composition to the surface of the polymeric fabric.

More particularly, the co-wetting aid has a surface tension within the range from about 20 to about 30 dynes/cm and the aqueous composition has a surface tension within the range from about 25 to about 50 dynes/cm. Suitable wetting aids include silicone polyethers and primary and secondary alcohols having 1 to 8 carbon atoms.

Alternatively, instead of adding the co-wetting aid to the aqueous composition containing the succinate surfactant, the co-wetting aid can be added to the polymer from which the strands of the polymeric fabric are made. In this embodiment, the co-wetting aid is dispersed in the fabric polymer and surface segregates to the surface of the strands and thus the surface of the fabric. The co-wetting aid reduces the apparent surface free energy of the fabric and is present on the fabric surface in an amount sufficient so that the succinate surfactant is uniformly distributed on the surface of the fabric. In this embodiment, suitable co-wetting aids include silicone polyethers but not primary and secondary alcohols having 1 to 8 carbon atoms.

According to another embodiment of the present invention, a polymeric fabric having enhanced wettability comprises a normally water repelling polymeric fabric having a surface, a first surfactant on the surface of the fabric having a cloud point less than about 50° C. and a low solubility in water and being dispersible in water, and a second surfactant on the surface of the fabric comprising a sorbitol succinate surfactant. Although the foregoing first and second surfactants are effective when used alone to enhance the wettability of polymeric fabric, the combination of the first and second surfactants is a more durable treatment. In other words, the fabric treated with both the first and second surfactants in accordance with the present invention remains wettable after more washings than fabric treated with either the first or second surfactant alone.

The first and second surfactants can be applied with a composition comprising the first surfactant, the second surfactant and water. More particularly, this composition of the present invention may include a co-wetting aid functional to wet the polymeric fabric with the composition during application of the composition to the polymeric fabric. The co-wetting aid is present in the composition in an amount sufficient to provide for substantially uniform distribution of the surfactants onto the polymeric fabric.

Suitable first surfactants have a cloud point of less than about 50° C. and include organosilicones, polyethylene oxides, and polyalkylene-oxide modified castor oil. More particularly, the suitable first surfactants include polyalkylene-oxide modified siloxanes. Preferably, the first surfactant comprises polyalkylene-oxide modified polydimethylsiloxane.

As with the first embodiment, suitable succinate surfactants include ethoxylated amino sorbitol succinate salt and alkenyl succinate anhydride ethoxylated fatty amine salt.

Suitable co-wetting aids include, but are not limited to, primary alcohols and secondary alcohols. Hexanol is a particularly suitable co-wetting aid.

In a preferred embodiment, the polymeric fabric of the present invention includes the first surfactant in an effective amount up to about 3% by weight of the fabric and the second surfactant in an effective amount up to about 3% by weight of the fabric. Preferably, the polymeric fabric of the present invention includes the first surfactant in an amount from about 0.1 to about 3% by weight of the fabric and the second surfactant in an amount from about 0.1 to about 3% by weight of the fabric. Most preferably, the polymeric fabric is a nonwoven polymeric fabric comprising polymeric strands such as fibers or filaments, or both.

Still further objects and the broad scope of applicability of the present invention will become apparent to those of skill in the art from the details given hereinafter. However, it should be understood that the detailed description of the preferred embodiments of the present invention is only given by way of illustration because various changes and modifications well within the spirit and scope of the invention should become apparent to those of skill in the art in view of the following detailed description.

DETAILED DESCRIPTION OF THE DRAWINGS

Figure 1:
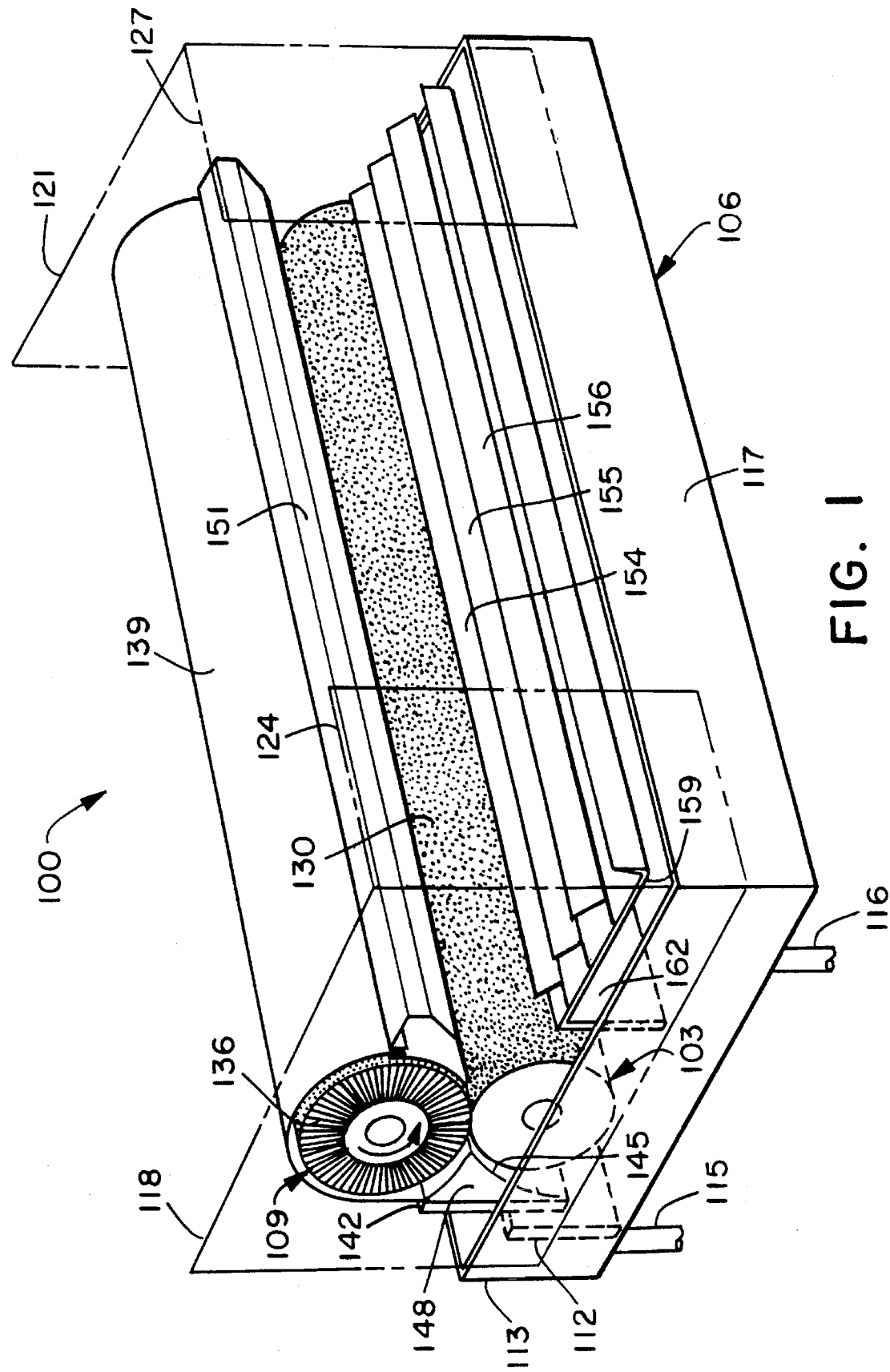
FIG. 1 is a perspective view of a brush spray applicator for use in applying the surface treatment to a nonwoven material in accordance with an embodiment of the present invention. A portion of the brush spray applicator is shown in phantom lines so that the rolls are visible.

The present invention provides polymeric fabric having enhanced wettability, methods for producing such wettable polymeric fabric, compositions for use in the method, and articles made with the treated fabric. The polymeric fabrics of the present invention are suitable to make absorbent products such as towels, wipes and absorbent personal care products including infant care items such as diapers, child care items such as training pants, feminine care items such as sanitary napkins, and adult care items such as incontinence products. The treated fabric of the present invention is particularly suitable for making disposable diapers and is especially suitable for making the liner and surge or fluid handling layers of a disposable diaper.

Types of polymeric fabrics which are particularly useful when surface treated according to the present invention include polyolefin nonwoven fabrics because such fabrics exhibit good absorbency characteristics and are relatively economically produced. Common polyolefin nonwoven fabrics include polypropylene and polyethylene spunbonded fabrics. Such fabrics are typically produced by processes disclosed in the following patents: U.S. Pat. No. 4,340,563 to Appel et al., U.S. Pat. No. 3,692,618 to Dorschner et al., U.S. Pat. No. 3,338,992 to Kinney, U.S. Pat. No. 3,341,394 to Kinney, U.S. Pat. No. 3,502,538 to Levy, U.S. Pat. No. 3,502,763 to Hartmann, U.S. Pat. No. 3,909,009 to Hartmann, U.S. Pat. No. 3,542,615 to Dobo et al., and Canadian Patent Number 803,714 to Harmon. Nonwoven bicomponent polymeric fabrics are particularly useful when surface treated according to the present invention. Nonwoven bicomponent fabrics are typically produced by processes such as are disclosed in U.S. Pat. No. 3,423,266 to Davies et al. and U.S. Pat. No. 3,595,731 to Davies, et al. These polymeric nonwovens show substantially improved wettability when treated in accordance with the present invention as described below.

The wettability of a normally water repelling polymeric fabric is enhanced according to the present invention by the application of succinate surfactant to the surface of the polymeric fabric. The surface of the fabric is actually formed by the surfaces of the polymeric strands from which the fabric is composed. Thus, the surfactant is applied to the surfaces of those strands which form the fabric surface. The term strands is meant to encompass fibers, which are cut or discontinuous strands having a definite length, and filaments, which are continuous strands of material.

More particularly, according to one embodiment of the present invention, the succinate surfactant is applied to the surface of the fabric in an aqueous composition which includes a co-wetting aid. The co-wetting aid reduces the surface tension of the aqueous composition containing the succinate surfactant and is present in the composition in an amount so that the succinate surfactant can be uniformly distributed on the surface of the polymeric fabric. Preferably, the co-wetting aid is present in the aqueous composition in an amount of at least about 0.02% by weight of the composition to achieve substantially uniform distribution of the succinate surfactant on the surface of the polymeric fabric. The succinate surfactant is present in the aqueous composition in an amount effective to enhance the wettability of the polymeric fabric. Likewise, the succinate surfactant is present on the surface of the treated polymeric fabric in an amount effective to render the fabric wettable. The succinate surfactant is preferably present in an amount up to about 3.0% by weight of the fabric and more preferably in an amount from about 0.1 to about 3.0% by weight of the fabric.

Suitable succinate surfactants include ethoxylated amino succinate salts and alkenyl succinate anhydride ethoxylated fatty amine salts. Preferably, the succinate surfactant has the following chemical formula:

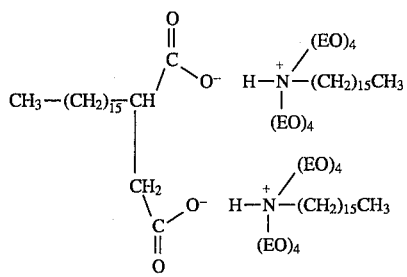

wherein EO is ethylene oxide.

Suitable co-wetting aids have a surface tension which is less than the apparent surface free energy of the polymeric fabric. For example, untreated polypropylene fabric typically has an apparent surface tree energy of about 36 dynes/cm. For application to most polymeric fabrics, the co-wetting aid is added to the composition in an amount sufficient to lower the surface tension of the composition to within the range from about 25 to about 50 dynes/cm.

Suitable silicone polyethers for use as co-wetting aids include three basic types A, B, and C whose chemical formulas are shown below.

Type A silicone polymers have the formula:

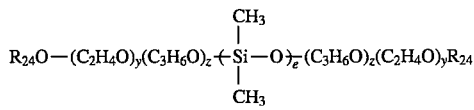

wherein $R_{24}$ is a hydrogen or an alkyl group such as a methyl or n-butyl group, y is a number from about 3 to about 16, z is a number from about 3 to about 60. A commercially available silicone polyether of type A is PS-071 available from Union Carbide Corporation of Danbury, Conn.

Type B silicone polymers have the formula:

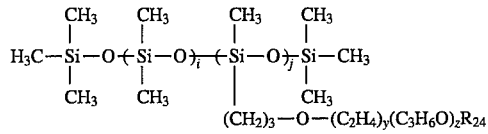

wherein, $R_{24}$ is a hydrogen atom or an alkyl group such as methyl or n-butyl, i is a number from about 0 to about 43, j is a number from about 1 to 5, y is a number from about 3 to 22, and z is a number from about 0 to 23. A commercially available silicone polyether of type B is Y-12230 polyalkylene oxide modified polydimethyl siloxane available from Union Carbide Corporation of Danbury, Conn.

Type C silicone polyether has the formula:

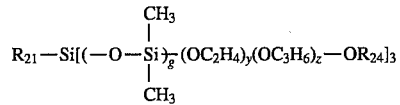

wherein, $R_{21}$ and $R_{24}$ are hydrogen atoms or an alkyl group such as methyl or n-butyl. Information on the range of values for g, y, and z was not available. A suitable silicone polyether of type C includes L-720 silicone polyether available from Union Carbide Corporation of Danbury, Conn.

Suitable alcohols for use as a co-wetting aid for sorbitol succinate surfactants include primary and secondary alcohols. A particularly suitable alcohol is hexanol.

The wettability of polymeric fabric is enhanced according to another embodiment of the present invention by applying multiple surfactants to the surface of the polymeric fabric. The combination of surfactants is a more durable treatment than either of the surfactants used alone. Generally described, the wettable polymeric fabric of the present invention is surface treated with a first surfactant that has a cloud point less than about 50° C. and a low solubility in water and is dispersible in water and a second surfactant comprising a sorbitol succinate surfactant. The cloud point is the temperature at which aqueous solutions of the surfactant become cloudy when cooled at a specific rate. The cloud point data provided herein was measured using a 1% solution of the surfactant in water.

Suitable first surfactants include organosilicones, polyethylene oxides, and polyalkylene-oxide modified castor oil. Preferred organosilicones include polyalkylene-oxide modified siloxanes. Polyalkylene-oxide modified castor oil is a castor oil having one or more polyalkylene-oxide groups attached to the main carbon chain of the castor oil. Likewise, polyalkylene-oxide modified siloxanes are siloxanes having polyalkylene-oxide groups attached to the main carbon chain of the siloxanes. These polyalkylene-oxide modifications are well know to those skilled in the art. A particularly preferred first surfactant is Y-12230 polyalkylene-oxide modified polydimethyl siloxane available from Union Carbide. Another suitable first surfactant is Mapeg CO-8 ethoxylated ester of castor oil from PPG of Gurnee, Ill.

Suitable second (succinate) surfactants, as with the previously described embodiment, include ethoxylated amino sorbitol succinate salts and alkenyl succinate anhydride ethoxylated fatty amine salts preferably having the chemical formula shown above.

The first and second surfactants are applied to polymeric fabric as a composition comprising the first surfactant, the second surfactant, and water. According to a preferred embodiment of the present invention, the first and second surfactants are applied to polymeric fabric as an aqueous composition including a co-wetting aid which is functional to wet the polymeric fabric with the composition during application of the composition to the polymeric fabric. The co-wetting aid is preferably present in the composition in an amount sufficient to provide for substantially uniform distribution of the first and second surfactants onto the polymeric fabric. Particularly suitable co-wetting aids include primary and secondary alcohols. Most primary and secondary alcohols and water azeotrope and evaporate relatively easily during the drying process so that the primary and secondary alcohols are substantially and completely evaporated from the treated polymeric fabric during drying. The surface treatment composition of the present invention preferably includes the co-wetting aid in an amount from about 0.05 to about 0.6% by weight of the composition. A particularly preferred co-wetting aid is hexanol. The first and second surfactants can be applied simultaneously in the same aqueous solution or can be applied separately, one after the other.

The wettable polymeric fabric of the present invention preferably comprises the first surfactant in an effective amount up to about 3% by weight of the wettable polymeric fabric and the second surfactant in an effective amount up to about 3.0% by weight of the wettable polymeric fabric. More preferably, the wettable polymeric fabric of the present invention comprises the first surfactant in an amount from about 0.1 to about 3% by weight of the wettable polymeric fabric and the second surfactant in an amount of from 0.1 to about 3.0% by weight of the wettable polymeric fabric.

Surface treatment processes within the scope of the present invention include printing and spraying methods and also a method whereby the co-wetting aid, or, in the second embodiment described above, the first surfactant (having a cloud point less than 50° C.), is internally incorporated into the fabric polymers which form the polymeric strands of the fabric and then surface segregates through the polymer to the surfaces of the strands and thus the fabric surface. In the latter method, the succinate surfactant is applied by printing or spraying or the like. Suitable printing and spraying methods include those disclosed in U.S. Pat. No. 5,057,361, the disclosure of which is incorporated herein by reference. A suitable brush spray application is disclosed in a U.S. patent application filed on Oct. 30, 1992 and entitled "Method Of Applying A Coating At High Bath Concentration And Low Wet Pick-Up To Materials Such As Nonwovens Using A Brush Spray Applicator." The brush spray applicator is described in detail below with reference to FIG. 1 and FIG. 2. However, it should be understood that the practice of the present invention is not limited to the above-described methods.

Figure 2:
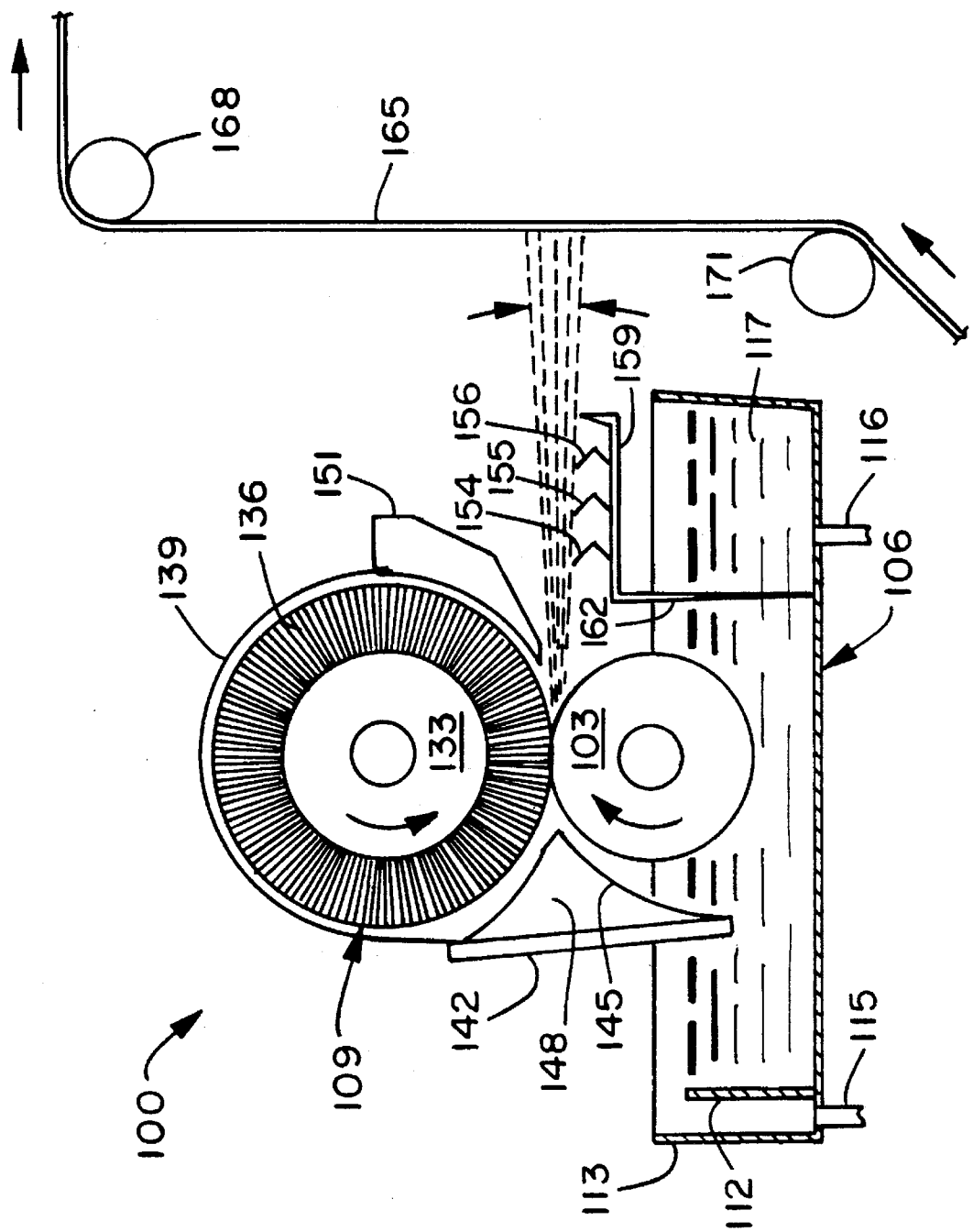
FIG. 2 is a partial schematic side elevation view of the brush spray applicator shown in FIG. 1.

A brush spray applicator 100 used in the brush spray application method of the present invention is shown in FIGS. 1 and 2 and generally comprises a pick-up roll 103 disposed in a bath container 106 and a bristle roll 109 positioned juxtapositional to the pick-up roll.

The bath container 106 has an elongated trough shape and is open at the top. A weir 112 extends along the length the bath container 106 proximate the rearward side 113 of the container. The weir 112 is spaced slightly from the rearward side 113 of the bath container 106 and controls the height of the bath in the bath container. A fluid outlet 115 extends from the bottom of the bath container 106 between the weir 112 and the rearward side 113 of the container and a fluid inlet 116 extends from the bottom of the bath container between the weir 112 and the forward side 117 of the bath container. The level of the bath in the bath container 106 is kept constant by recirculating the bath in the container. Fluid enters the bath container through the fluid inlet 116, flows over the weir 112, and exits the bath container through the fluid outlet 115. The fluid inlet 116 and outlet 115 may be connected to a fluid source such as a storage tank (not shown).

The pick-up roll 103 and bristle roll 109 extend between L-shaped support panels 118 and 121 which fit against interior sidewalls of the bath container 106. One of the support panels 118 is shown in phantom so that the pick-up roll 103 and bristle roll 109 are visible. The support panels 118 and 121 extend below the upper edge of the weir 112 and above the bristle roll 109. The support panels 118 and 121 each have frontal portions 124 and 127 which extend inwardly along the forward side 117 of the bath container 106. The pick-up roll 103 and bristle roll 109 are rotatably mounted in hubs (not shown) in the support panels 117 and 118. In addition to supporting the pick-up roll 103 and bristle roll 109, the support panels 118 and 121 function as a spray shield to prevent fluid spray from escaping from the ends of the brush spray applicator 100. The support panels 118 and 121 also inhibit air circulation about the pick-up roll 103 and bristle roll 109.

The pick-up roll 103 is positioned to extend partially above the bath container 106 and is partially submerged in the bath in the bath container. The pick-up roll 103 preferably has a shot-peened outer surface 130 for improved liquid pick-up and is crowned to allow for deflection of the pick-up roll and bristle roll 109 along their lengths.

The bristle roll 109 includes a core 133 which extends between the support panels 118 and 121 and an array of bristles 136 extending from the core. The bristles 136 are preferably from 1.2 to 1.75 inches (3.0–4.4 cm) long. The bristle roll 109 is positionable so that the ends of the bristles 136 contact the outer surface 130 of the pick-up roll 103 as the bristle roll rotates. Preferably the bristle roll 109 is adjustable so that the length of the portion of the bristles 136 contacting the outer surface 130 of the pick-up roll 103 is variable. It is also desirable that the bristle roll 109 be adjustable so that the bristle roll 109 can be disengaged from the pick-up roll 103. The dimensions of the bristles 136 and the materials from which the materials are made may vary, but the bristles should be capable of deflecting when contacting the pick-up roll 103 and then have enough resilience to spring to the original shape of the bristles and project fluid from the surface of the pick-up roll to form a spray of atomized fluid droplets.

The degree of interference between the bristles 136 and the outer surface 130 of the pick-up roll 103 is the length of the bristles which extends from the end of the bristles towards the core 133 of the bristle roll 109 and contacts the outer surface of the pick-up roll as the bristles pass over the outer surface of the bristle roll. The degree of interference between the bristles 136 of the bristle roll 109 and the pick-up roll 103 preferably ranges from about 0.01 to about 0.03 inches (0.025–0.076 cm). The strip of contact along the outer surface 130 of the pick-up roll 103 between the outer surface and the bristles 136 of the bristle roll 109 also may vary but is preferably about ½ inch wide.

A spray shield 139 extends between the support panels 118 and 121 and over the bristle roll 109. A rearward shield 142 extends from the rearward edge of the spray shield 139 into the bath container 106 to a level below the upper edge of the weir 112 so that the lower edge of the rearward shield is below the level of the bath in the bath container. The rearward shield 142 also extends between the support panels 118 and 121. An air stripping doctor 145 extends along the rearward side of the pick-up roll 103 and is connected to the rearward shield 142 by air baffles 148. The air stripping doctor 145, air baffles 148 and rearward shield 142 inhibit the circulation of air about the pick-up roll 103 and bristle roll 109.

An upper fluid stripping doctor 151 extends from the forward edge of the spray shield 139 towards the nip between the pick-up roll 103 and bristle roll 109. A series of lower fluid stripping doctors 154, 155 and 156 are mounted on a platform 159 extending from proximate the nip between the pick-up roll 103 and the bristle roll 109 over and beyond the forward side 117 of the bath container 106. The lower fluid stripping doctors 154, 155 and 156 are V-shaped and extend between the frontal portions 124 and 127 of the support panels 118 and 121. The lower fluid stripping doctor platform 159 has a vertical leg which extends from proximate the nip between the pick-up roll 103 and bristle roll 109 into the bath container 106 to a lower edge below the upper edge of the weir 112 so that the platform 159 extends into the bath in the bath container. The upper fluid stripping doctor 151 and the lower fluid stripping doctors 154, 155, and 156 control the path and angle of the fluid spray emitted from the nip between the pick-up roll 103 and bristle roll 109 and also aid in inhibiting the circulation of air about the pick-up roll and bristle roll. The upper fluid stripping doctor 151 and the lower fluid stripping doctors 154, 155 and 156 may be set in various positions but preferably are positioned so that the coating solution spray emitted from the nip between the pick-up roll 103 and bristle roll 109 has a spray angle from about 10° to about 20° and most preferably 15°. As shown in FIG. 2, during operation of the brush spray applicator 100, the material to be treated, such as a nonwoven web 165, is passed over rollers 168 and 171 and through the path of fluid spray emitted from the brush spray applicator.

During operation of the brush spray applicator 100, a coating solution is introduced into the bath container 106 through the fluid inlet 116 and as explained above is continuously recirculated so that the weir 112 maintains the bath at a constant level. The pick-up roll 103 and bristle roll 109 are rotated at different speeds by a motor which is not shown. The speeds of the pick-up roll 103 and bristle roll 109 may vary considerably depending on the factors such as the bath viscosity, the nature of the bristles 136 of the bristle roll 109, and the desired rate of application of the coating solution. However, the pick-up roll 103 is preferably operated at a speed from about 1.5 to about 15 rpm and the bristle roll is preferably rotated at a speed from about 480 to about 1200 rpm. Preferably, the bristle roll is capable of operating at a velocity sufficient so that the coating solution can penetrate the material being treated, and more preferably, penetrates the material from the one side of the material facing the spray to the opposite side of the material. The line speed of the material being treated can also vary considerably but preferably varies between 135 and 1750 feet per minute (41–533 meters per minute).

The nonwoven material 165 is preferably a hydrophobic, nonwoven spunbonded web having a basis weight from about 0.5 to about 1.5 ounces per square yard (16.8–50.4 grams per square meter) and higher. Such material is well known in the art and may be prepared in a conventional fashion in accordance with the patents identified above.

As mentioned above, the co-wetting aid or the first surfactant (having a cloud point less than 50° C.) can be internally incorporated into the polymer from which the polymeric strands forming the fabric are made. The co-wetting aid or first surfactant must be one that surface segregates from inside the polymeric strands to the outer surfaces of the strands and thus the surface of the fabric. One such material is trisiloxane polyether having the following formula:

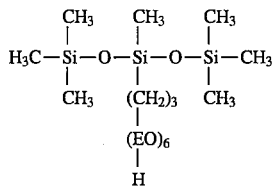

wherein EO is ethylene oxide.

Methods for internal incorporation of co-wetting aids and surfactants into the polymer from which a polymeric fabric is made are disclosed in U.S. Pat. Nos. 4,857,251; 5,057,262; 5,114,646; and 5,120,888, the disclosures of which are expressly incorporated herein by reference.

The following Examples 1–10 are designed to illustrate particular embodiments of the present invention and teach one of ordinary skill in the art how to carry out the present invention. The following Comparative Examples 1–6 are designed to illustrate advantages of the present invention.

EXAMPLE 1

The ability of aqueous compositions comprising succinate surfactant to wet-out on nonwoven polypropylene fabric was evaluated by adding gradually increasing amounts of silicone polyether to aqueous compositions comprising succinate surfactant and then applying the composition to the surface of the fabric. The succinate surfactant (SS) was alkenyl succinate anhydride ethoxylated fatty amine salt having the following formula:

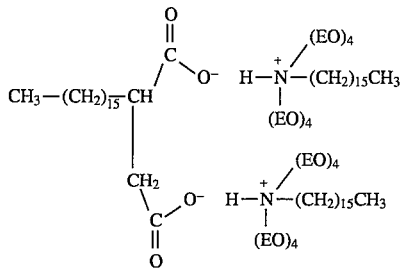

wherein EO is ethylene oxide.

The silicone polyether was PS-071 silicone polyether available from Huls of Piscataway, N.J. The contents of the aqueous compositions are shown in Table 1 along with the surface tension of the compositions and an indication of the ability of the compositions to wet the fabric. The ability of the compositions to wet the fabric was obtained from a visual observation. The surface tensions were measured using a Tensiometer available from Fisher Scientific. The apparent surface free energy of the polypropylene fabric was about 36 dynes/cm. The ability of the compositions to wet the fabric is indicated as poor or good. From the results in Table 1, it can be seen that the minimum concentration of silicone polyether to achieve good wet-out on polypropylene fabric is between 14.5 and 29 mg per 100 ml or about 0.02% by weight.

TABLE 1

| Sample | 1 | 2 | 3 | 4 | 5 | 6 |
|---|---|---|---|---|---|---|
| water (ml) | 100 | 100 | 100 | 100 | 100 | 100 |
| SS (% weight) | 0.5 | 2 | 2 | 2 | 2 | 2 |
| PS-071 (mg) | 0 | 0 | 14.5 | 29 | 43.5 | 58 |
| surface tension (dynes/cm) | 33 | 33 | 32 | 30 | 29 | 28–29 |
| wet-out | poor | poor | poor | good | good | good |

EXAMPLE 2

A 0.7 osy (24 gsm) polypropylene spunbond fabric was treated with a surfactant bath using a nozzle spray apparatus as disclosed in U.S. Pat. No. 5,057,311. The treatment bath comprised 2% by weight alkenyl succinate anhydride ethoxylated fatty amine salt and 0.03% by weight silicone polyether, with the remainder being water. The alkenyl succinate anhydride ethoxylated fatty amine salt had the chemical formula shown in Example 1 and the silicone polyether had the following chemical formula:

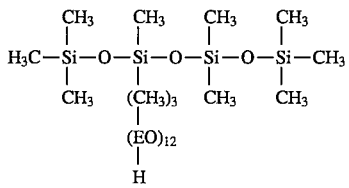

wherein EO is ethylene oxide.

The fabric was dried and the dry add-on weight as a result of the treatment was 0.94–0.96% by weight of the fabric. The resulting treated fabric was subjected to a water run-off test to evaluate the durability of the surfactant treatment. The run-off test was performed with the following procedure:

A 6 inch by 6 inch (15×15 cm) piece of treated fabric was placed flat on top of an absorbent medium which was positioned at a 30° incline plane. A funnel was placed above the fabric. 100 milliliters of distilled water at about 35° C. was dispensed from the funnel onto the fabric over a time period of about 15 seconds. Any of the distilled water that was not absorbed by the fabric ran off the fabric and was collected. The volume of run-off was measured. The samples of the fabric were repeatedly subjected to the run-off test and then washed until the amount of run-off water from the run-off test exceeded 20 milliliters. 6 wash cycles were required for the run-off test to exceed 20 milliliters. The fabric samples were washed by stirring the fabric in 1000 ml of tap water for 3 hours.

EXAMPLE 3

Figure 3:
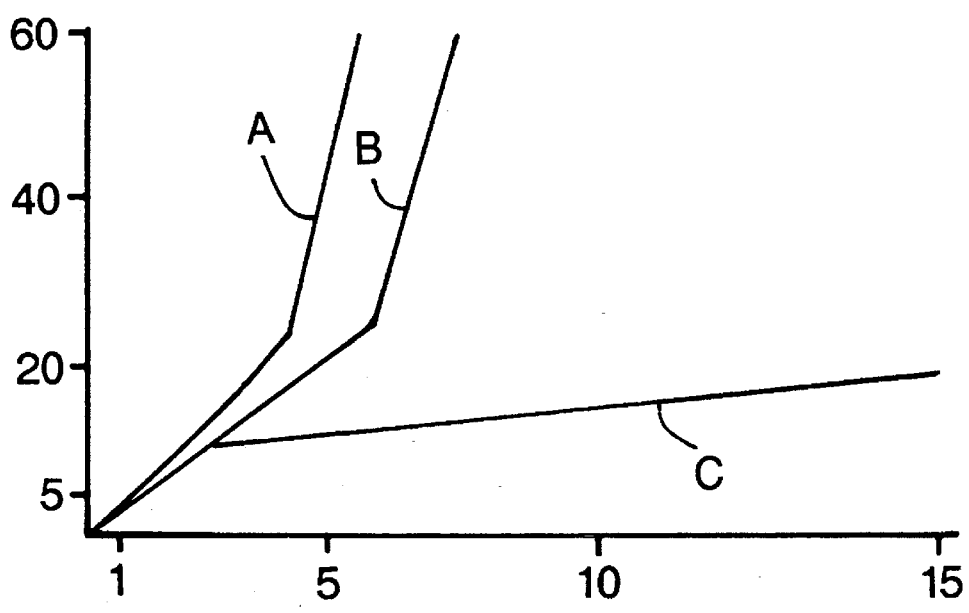
FIG. 3 is a graph comparing the durability of a surface treatment applied to a nonwoven fabric in accordance with an embodiment of the present invention with the durability of conventional surface treatments.

Three samples A, B, and C, of 0.8 osy (27 gsm) spunbond polypropylene fabric were treated with surfactant compositions by dipping the samples in the compositions. Sample A was treated with an aqueous composition comprising Triton X-102 surfactant available from Rohm and Haas and the resulting dry add-on weight of the surfactant was 0.7% by weight of the fabric. Sample B was treated with an aqueous composition comprising trisiloxane polyether and the resulting dry add-on weight of the surfactant was 1% by weight of the fabric. Sample C contained 1.0% by weight trisiloxane polyether present on the polypropylene fabric fiber surface through surface segregation and was treated with an aqueous composition comprising alkenyl succinate anhydride ethoxylated fatty amine salt having the same chemical formula as shown in Example 1. The dry add-on of the alkenyl succinate anhydride ethoxylated fatty amine salt was 0.7% by weight of the fabric. The three samples were repeatedly subjected to 60 ml water insults and with each insult the time for penetration of the water was measured. The results are graphically shown in FIG. 3. As can be seen, sample C treated with trisiloxane polyether and succinate surfactant remained wettable for significantly more insults than samples A and B.

EXAMPLE 4

A through-air bonded polypropylene/polyethylene bicomponent spunbond nonwoven fabric having a basis weight of 1.5 osy (50 gsm), a thickness of 0.05 inches (0.13 cm), and filaments of 4 denier was treated with the brush spray applicator system 100 described above and shown in FIGS. 1 and 2. The treatment bath comprised multiple surfactants, 10% by weight of a first surfactant, Y-12230 polyalkylene-oxide dimethyl siloxane available from Union Carbide, 25% by weight of a second surfactant, the alkenyl succinate anhydride ethoxylated fatty amine salt having the formula shown in Example 1, and 65% by weight water. The fabric was treated at a line speed of 135 feet per minute (41 meters per minute) and was through-air dried at a temperature of 240° F. (115° C.).

The pick-up roll 103 was made of stainless steel with a 100 rms finish and had a 6.375 inch (16.2 cm) diameter. The pick-up roll 103 was rotated at 3.2 rpm. The brush roll 109 had a total diameter of 10⁷⁄₁₆ inches (26.5 cm) and white nylon bristles that were 1⅜ inches (3.5 cm) long with a diameter of 0.012 inches (0.030 cm). The bristle roll 109 was rotated at 850 rpm. The degree of interference between the bristles 136 of the bristle roll 109 and the outer surface 130 of the pick-up roll 103 was 0.015 inches (0.038 cm) and the clearance between the bristle roll and the spray shield 139 was ¹⁄₁₆ inch (0.16 cm). The clearance between the upper fluid stripping doctor 151 and the bristle roll was ¹⁄₁₆ inch (0.16 cm) at the heel and 0.015 inches (0.038 cm) at the tip. The lower fluid stripping doctors 154, 155, and 156 were located ⅛ inch (0.32 cm) below the top of the pick-up roll 103. The air baffles 148 were spaced 6 inches (15 cm) apart and the clearance between the air baffles and the bristle roll was ¹⁄₃₂ inch (0.08 cm). The bath in the bath container 106 was recirculated between the bath container and a recirculation tank at a rate of 5 gallons per minute (19 liters per minute). The level of the bath was maintained such that the pick-up roll 103 was submerged 2.25 inches into the bath. The strip of contact between the outer surface 130 of the pick-up roll 103 and the bristles 136 of the bristle roll 109 was about ½ inch (1.3 cm) wide. The resulting spray from the bristle roll 109 was controlled to a 15 degree pattern by the upper fluid stripping doctor 151 and the lower fluid stripping doctors 154, 155 and 156. The nonwoven web was directed vertically and upwardly with respect to the brush spray applicator system 100 at a distance of ¼ inches (0.64 cm) from the outermost portion of the lower fluid stripping doctor platform 159 and 8¼ inches (21 cm) from the nip between the pick-up roll 103 and the bristle roll 109.

EXAMPLE 5

A through-air bonded 50/50 side by side polypropylene/polyethylene bicomponent spunbond nonwoven fabric having a basis weight of 1.5 osy (50 gsm) and filaments of 4 denier was treated with a surfactant bath using a nozzle spray apparatus as disclosed in U.S. Pat. No. 5,057,361. A treatment bath comprising 0.53% by weight of a first surfactant, Y-12230 polyalkylene-oxide dimethyl siloxane available from Union Carbide, 1.33% by weight of a second surfactant, the alkenyl succinate anhydride ethoxylated fatty amine salt having the formula shown in Example 1, with the remainder being water. The fabric was treated at a line speed of 80 feet per minute (24 meters per minute) and was through-air dried at a temperature of 250° F. (121° C.).

Samples of the treated fabrics from Examples 4 and 5 were evaluated and results are shown in Table 2. The wet pick-up is shown in percent by weight of the web fabric and is the amount of bath added to the fabric before drying. The surfactant dry add-on is the amount of surfactant added to the dried treated fabric in percent by weight of the dry treated fabric. The run-off test was performed with the following procedure:

A 5 inch by 15 inch (13×38 cm) piece of a treated fabric was placed flat on top of an absorbent medium which was positioned at a 30° incline plane. A funnel was placed above the fabric. 100 millimeters of distilled water at about 35° C. was dispensed from the funnel onto the fabric over a time period of about 15 seconds. Any of the distilled water that was not absorbed by the fabric ran off the fabric and was collected. The volume of run-off water was measured.

The samples of fabric were repeatedly subjected to the run-off test and then washed until the amount of run-off water from the run-off test exceeded 20 milliliters. The number of cycles required for the run-off test to exceed 20 milliliters is shown in Table 2. The fabric samples were washed by submerging the samples in 500 milliliters of water at 25° C. and than agitating the samples in the water for 1 minute. The washed samples were then dried in a oven at 200° F. (93° C.) for 8 minutes.

TABLE 2

|  | Example 4 | Example 5 |
| --- | --- | --- |
| Basis Weight (osy) | 1.5 | 1.5 |
| Basis Weight (gsm) | 50 | 50 |
| First Surfactant Dry Add-On, % | 0.4 | 0.4 |
| Second Surfactant Dry Add-On, % | 1.0 | 1.0 |
| Wet PickUp % | 4.0 | 75 |
| Wash/Runoff Cycles | 6 | 7 |

As can be seen from the data shown in Table 2, the fabric sample from Example 4 treated in accordance with the present invention remained hydrophilic for up to 6 wash cycles and had a wet pick-up of only 4% by weight. The fabric sample from Example 5 wherein the surfactant was applied with a nozzle spray remained hydrophilic for up to 7 wash cycles but had a wet pick-up of 75% by weight after treatment. The line speed for Example 4 was considerably faster than of Example 5 because the drying time for the sample from Example 4 was significantly less than that for compared to Example 5 due to the low wet pick-up of the fabric from Example 4.

EXAMPLE 6

A through-air bonded 50/50 side by side polypropylene/polyethylene bicomponent spunbond nonwoven fabric having a basis weight of 1.5 osy (50 gsm) and filaments of 4 denier was treated with successive surfactant baths using a nozzle spray apparatus as disclosed in U.S. Pat. No. 5,057,361. A first treatment bath comprising 1.33% by weight alkenyl succinate anhydride ethoxylated fatty amine salt having the formula shown in Example 1, with the remainder being water, was applied to the surface of the fabric at a line speed of 80 feet per minute (24 meters per minute). A second treatment bath comprising 0.53% by weight Y-12230 polyalkylene-oxide dimethyl siloxane available from Union Carbide and 0.3% by weight hexanol, with the remainder being water, was then applied to the surface of the fabric at the same line speed. The treated fabric was through-air dried at a temperature of 250° F. (121° C.).

EXAMPLE 7

Example 6 was repeated except that the order of application of the first and second baths was reversed.

EXAMPLE 8

Example 6 was repeated except that the fabric being treated comprised homofilaments of polypropylene instead of bicomponent filaments.

EXAMPLE 9

Example 6 was repeated except that the second treatment bath comprised 0.53% by weight Mapeg CO-8 ethoxylated ester of castor oil from PPG of Gurnee, Ill., instead of Y-12230.

EXAMPLE 10

Example 9 was repeated except that the order of application of the first and second treatment baths was reversed.

COMPARATIVE EXAMPLE 1

A through-air bonded 50/50 side by side polypropylene/polyethylene bicomponent spunbond nonwoven fabric having a basis weight of 1.5 osy (50 gsm) and filaments of 4 denier was treated with a single surfactant bath using a nozzle spray apparatus as disclosed in U.S. Pat. No. 5,057,361. The treatment bath comprised 1.33% by weight alkenyl succinate anhydride ethoxylated fatty amine salt having the formula shown in Example 1, with the remainder being water, and was applied to the surface of the fabric at a line speed of 80 feet per minute (24 meters per minute). The treated fabric was through-air dried at a temperature of 250° F. (121° C.).

COMPARATIVE EXAMPLE 2

Comparative Example 1 was repeated except that the treatment bath comprised 0.53% by weight Y-12230 polyalkylene-oxide dimethyl siloxane available from Union Carbide and 0.3% by weight hexanol, with the remainder being water.

COMPARATIVE EXAMPLE 3

Comparative Example 1 was repeated except that the treatment bath comprised 0.53% by weight Mapeg CO-8 ethoxylated ester of castor oil available from PPG, of Gurnee, Ill., with the remainder being water.

COMPARATIVE EXAMPLE 4

Comparative Example 1 was repeated except that the treatment comprised 1.87% by weight alkenyl succinate anhydride ethoxylated fatty amine salt having the formula shown in Example 1, with the remainder being water.

COMPARATIVE EXAMPLE 5

Comparative Example 1 was repeated except that the treatment comprised 1.87% by weight Y-12230 and 0.3% by weight hexanol, with the remainder being water.

COMPARATIVE EXAMPLE 6

Comparative Example 1 was repeated except that the treatment comprised 1.87% by weight Mapeg CO-8, with the remainder being water.

Samples of the treated fabrics from Examples 6–10 and Comparative Examples 1–6 were evaluated and results are shown in Table 3. The amounts of the surfactants in the baths are shown in percent weight and the succinate surfactant is identified as "SS". The dry add-on is the amount of surfactant added to the dried treated fabric in percent by weight of the dry treated fabric. The run-off test was performed with the same procedure described above with regard to Examples 4–10 and the results are shown in number of wash cycles survived.

TABLE 3

| EXAMPLE | First Surfactant Bath | | | Second Surfactant Bath | | | WASH CYCLES |
|---|---|---|---|---|---|---|---|
| | SURFACTANT | BATH CONCENTRATION % | DRY ADD-ON % | SURFACTANT | BATH CONCENTRATION % | DRY ADD-ON % | |
| 6 | SS | 1.33 | 1.0 | Y-12230 | 0.53 | 0.4 | 9 |
| 7 | Y-12230 | 0.53 | 0.4 | SS | 1.33 | 1.0 | 6 |
| 8 | SS | 1.33 | 1.0 | Y-12230 | 0.53 | 0.4 | 10 |
| 9 | SSS | 1.33 | 1.0 | MAPEG | 0.53 | 0.4 | 9 |
| 10 | MAPEG | 0.53 | 1.0 | SS | 1.33 | 1.0 | 7 |
| COMPARATIVE 1 | SS | 1.33 | 1.0 | — | — | — | 2 |
| COMPARATIVE 2 | Y-12230 | 0.53 | 0.4 | — | — | — | 3 |
| COMPARATIVE 3 | MAPEG | 0.53 | 0.4 | — | — | — | 4 |
| COMPARATIVE 4 | SSS | 1.87 | 1.4 | — | — | — | 3 |
| COMPARATIVE 5 | Y-12230 | 1.87 | 1.4 | — | — | — | 3 |
| COMPARATIVE 6 | MAPEG | 1.87 | 1.4 | — | — | — | 5 |

As can be seen from the data in Table 3, the multiple surfactant treatments used in Examples 6–10 were more durable than the single surfactant treatments of Comparative Examples 1–6. This was true even for Comparative Examples 4–6 wherein the single surfactant treatments were applied to provide a surface concentration equal to the total surfactant surface concentration applied by the multiple surfactant treatments of Examples 6–10.

The foregoing descriptions relates to preferred embodiments of the present invention, and modifications or alterations may be made without the departing from the spirit and scope of the invention as defined in the following claims.

We claim:

1. A wettable polymeric fabric capable of withstanding at least six washings under the water run-off test before run-off exceeds 20 milliliters comprising:

a polyolefin polymeric fabric having a first and second surfactant on a surface, each in an amount in the range of from about 0.1 to 3.0% by weight based on the fabric weight;

said fabric having been treated with a first surfactant having a cloud point less than about 50° C. and being dispersible in water; and said fabric having been treated with a second surfactant comprising a succinate surfactant.

2. A wettable polymeric fabric as in claim 1 wherein the second surfactant comprises an ethoxylated amino succinate salt.

3. A wettable polymeric fabric as in claim 1 wherein the second surfactant comprises alkenyl succinate anhydride ethoxylated fatty amine salt.

4. A wettable polymeric fabric as in claim 1 wherein the first surfactant is selected from the group consisting of organosilicones, polyethylene oxides, and polyalkylene oxide modified castor oil.

5. A wettable polymeric fabric as in claim 1 wherein the first surfactant comprises a polyalkylene oxide modified siloxane.

6. A wettable polymeric fabric as in claim 1 wherein the first surfactant comprises polyalkylene oxide modified polydimethyl siloxane.

7. A wettable polymeric fabric as in claim 1 wherein the polymeric fabric comprises nonwoven polymeric fabric.

8. A wettable polymeric fabric as in claim 1 wherein the second surfactant comprises an ethoxylated amino succinate salt and the first surfactant is selected from the group consisting of organosilicones, polyethylene oxides, and polyalkylene oxide modified castor oil.

9. A wettable polymeric fabric as in claim 1 wherein the second surfactant comprises an alkenyl succinate anhydride ethoxylated fatty amine salt and the first surfactant is selected from the group consisting of organosilicones, polyethylene oxides, and polyalkylene oxide modified castor oil.

10. A wettable polymeric fabric as in claim 1 wherein the second surfactant comprises an alkenyl succinate anhydride ethoxylated fatty amine salt and the first surfactant comprises polyalkylene oxide modified polydimethyl siloxane.

* * * * *

UNITED STATES PATENT AND TRADEMARK OFFICE
CERTIFICATE OF CORRECTION

PATENT NO. : 5,620,788
DATED : April 15, 1997
INVENTOR(S) : Garavaglia et al.

It is certified that error appears in the above-identified patent and that said Letters Patent is hereby corrected as shown below:

Column 2, Line 1, "need an" should read -- need for an --

Column 5, Line 18, "tree" should read -- free --

Column 5, Line 42, "$(C_2H_4)$" should read -- $(C_2H_4O)$ --

Column 6, Line 22, "know" should read -- known --

Column 15, Second Column Heading, "Surfactfant" should read --Surfactant --

Signed and Sealed this

Second Day of September, 1997

Attest:

BRUCE LEHMAN

*Attesting Officer*           *Commissioner of Patents and Trademarks*